US009029776B2

(12) United States Patent
Mäntylä

(10) Patent No.: US 9,029,776 B2
(45) Date of Patent: May 12, 2015

(54) DETERMINING THE AMOUNT OF STARCH

(75) Inventor: Markku Mäntylä, Kangasala (FI)

(73) Assignee: Metso Automation Oy, Helsinki (FI)

( * ) Notice: Subject to any disclaimer, the term of this patent is extended or adjusted under 35 U.S.C. 154(b) by 810 days.

(21) Appl. No.: 13/061,255

(22) PCT Filed: Sep. 5, 2008

(86) PCT No.: PCT/FI2008/050498
§ 371 (c)(1),
(2), (4) Date: May 6, 2011

(87) PCT Pub. No.: WO2010/026281
PCT Pub. Date: Mar. 11, 2010

(65) Prior Publication Data
US 2011/0204232 A1   Aug. 25, 2011

(51) Int. Cl.
G01N 21/35 (2014.01)
D21H 17/28 (2006.01)
D21H 19/54 (2006.01)
D21H 23/78 (2006.01)
G01N 33/34 (2006.01)
G01N 21/3563 (2014.01)
(Continued)

(52) U.S. Cl.
CPC .............. D21H 23/78 (2013.01); *D21H 17/28* (2013.01); *D21H 19/54* (2013.01); *D21H 23/56* (2013.01); G01N 33/346 (2013.01); *G01N 21/3559* (2013.01); G01N 21/3563 (2013.01); G01N 21/8422 (2013.01); *G01N 2021/8416* (2013.01); *G01N 2021/8427* (2013.01); *G01N 2021/8663* (2013.01); *G01N 2021/8433* (2013.01)

(58) Field of Classification Search
CPC ............ G01N 21/3563; G01N 33/346; G01N 21/3559; D21H 23/78; D21H 17/28; D21H 19/54; D21H 23/56
USPC .................................. 250/308, 338.1, 339.09
See application file for complete search history.

(56) References Cited

U.S. PATENT DOCUMENTS 4,845,730 A * 7/1989 Mercer ........................... 378/53
5,124,552 A * 6/1992 Anderson ................ 250/339.04
(Continued)

FOREIGN PATENT DOCUMENTS

CN   1474183 A   2/2004
CN   1590983 A   3/2005
(Continued)

OTHER PUBLICATIONS

International Search Report in International Application No. PCT/FI2008/050498; dated Jun. 3, 2009.
(Continued)

Primary Examiner — Mark R Gaworecki
(74) Attorney, Agent, or Firm — Oliff PLC

(57) ABSTRACT

The invention relates to a method and arrangement for determining the amount of starch used in surface-sizing a cellulose product. In the solution according to the invention, the amount of starch is determined with a transmission method utilizing IR spectroscopy by using absorption wavelengths of cellulose. Absorption values are measured before adding a coating and after it, whereby the amount of starch is determined from the difference between these absorption values.

12 Claims, 1 Drawing Sheet

(51) Int. Cl.
  *G01N 21/84* (2006.01)
  *D21H 23/56* (2006.01)
  *G01N 21/3559* (2014.01)
  *G01N 21/86* (2006.01)

(56) References Cited

U.S. PATENT DOCUMENTS

| | | | |
|---|---|---|---|
| 5,296,257 | A | 3/1994 | Knop et al. |
| 5,338,361 | A * | 8/1994 | Anderson et al. ............ 118/689 |
| 5,455,422 | A * | 10/1995 | Anderson et al. .......... 250/341.1 |
| 5,581,353 | A * | 12/1996 | Taylor ........................ 356/631 |
| 5,663,565 | A * | 9/1997 | Taylor ...................... 250/339.11 |
| 6,248,174 | B1 | 6/2001 | Kustermann |
| 6,355,931 | B1 * | 3/2002 | Hernandez et al. ........ 250/341.1 |
| 6,470,294 | B1 * | 10/2002 | Taylor ......................... 702/172 |
| 6,495,831 | B1 | 12/2002 | Hyvarinen et al. |
| 6,627,043 | B1 | 9/2003 | Mantyla |
| 2001/0055810 | A1 | 12/2001 | Carr et al. |
| 2003/0047135 | A1 | 3/2003 | Kansakoski et al. |
| 2005/0106312 | A1 * | 5/2005 | Mantyla ............................ 427/8 |

FOREIGN PATENT DOCUMENTS

| | | |
|---|---|---|
| EP | 0 272 645 | 6/1988 |
| EP | 0 518 393 A1 | 12/1992 |
| FI | 115412 B1 | 4/2005 |
| JP | A-03-160345 | 7/1991 |
| WO | WO 86/02162 A1 | 4/1986 |

OTHER PUBLICATIONS

Written Opinion of the International Searching Authority in International Application No. PCT/FI2008/050498; dated Jun. 3, 2009.
Aug. 31, 2012 Office Action issued in Chinese Patent Application No. 200880131506.9 (with translation).
"Extraction, Purification, Characterization and Content Determination of Starch and Amylose from *Canna edulis* Ker. Growing in China," 2008, vol. 29, No. 09, Zhang Juan et al (with abstract).
"Photometric Determination of Starch in Foodstuffs," *Part B: Chem. Anal.*, Zhang Maosheng et al. (with abstract).
May 8, 2014 Supplemental Search Report issued in European Patent Application No. 08805421.8.

* cited by examiner

DETERMINING THE AMOUNT OF STARCH

BACKGROUND OF THE INVENTION

The invention relates to a method of determining the amount of starch used in surface-sizing a cellulose product.

Further, the invention relates to an arrangement for determining the amount of starch used in coating a cellulose product.

In manufacturing cellulose products, properties of a product can be influenced by using what is called surface sizing. In surface sizing, the surface of a cellulose product is closed by adding interfibre bonds with water-soluble polymers, such as starch, to improve strength properties, facilitate further treatment and prevent dust formation, for example. In surface sizing, starch is typically applied to the surface of the cellulose product in very small amounts, for instance 0.5 to 2 $g/m^2$ either on one side or both sides of the paper. Surface sizing is typically used for, for instance, fine papers, raw papers to be coated and cardboards.

When determining properties and compositions of materials, one method generally in use is spectroscopy, which is based on analyzing radiation. In spectroscopy, radiation which is either radiated, absorbed or reflected by the object to be examined may be used according to the purpose of use. For different purposes, different wavelength ranges may be utilized, such as infrared radiation and ultraviolet radiation, and sectors of spectroscopy are correspondingly called infrared spectroscopy, i.e. IR spectroscopy, and ultra-violet spectroscopy, i.e. UV spectroscopy. Typically, many properties of cellulose products, such as the amount of actual coating, can be measured particularly by means of IR spectroscopy, as disclosed in patent publication FI 115 412, for example.

IR spectroscopy may be utilized when determining the composition of a material, for instance by measuring absorption of radiation, i.e. radiation absorbed by the material, at several wavelengths of infrared radiation. The absorbance of infrared radiation is proportional to the concentration of the absorbing substance in the sample, and the absorption peaks caused by the resonance frequencies of each particular chemical substance are located at wavelengths characteristic of the substance. Thus, the use of appropriate wavelengths enables determination of the composition and, for example, moisture of a cellulose product.

A problem in determining the amount of starch by utilizing spectroscopy is, however, that the absorption peak of starch is located substantially in the same wavelength range as the absorption peak of cellulose, due to which determining the amount of starch with a conventional application method of spectroscopy by direct measurement of the absorption value is not successful. One example of utilizing spectroscopy in determining the amount of starch-based size used for sizing layers of corrugated board is, however, disclosed in patent publication U.S. Pat. No. 5,663,565. When layers of corrugated board are sized, starch size is spread only at the ends of the folds on the contact surfaces to be sized, not evenly over the whole product surface. In the method of this publication, absorption values are measured in the absorption wavelength range of the water and/or starch contained by the size, and the signal part oscillating at the frequency of the folding is separated from the measurement signal, while the variations relating to something else than the amount of size are filtered. This method is not, however, applicable to measuring starch in surface sizing, where the intention is to spread starch evenly over the surface of a cellulose product. Further, the measuring inaccuracy of the method is great due to the number of factors affecting the measuring result.

Thus, in practice, measuring the amount of starch sufficiently accurately is almost impossible with the present measuring technology. Typically, the only method available in addition to the method of the abovementioned US publication is dry weight difference measurement, which determines the difference between the basis weight and the weight of water before adding surface size and after having added surface size, the amount of starch being determined on the basis of the difference between these two, i.e. on the basis of the dry weight difference. However, this method is problematic as well, because the error of measurement may, even with this method, easily rise to dozens of per cents of the amount of starch, which is typically very small as compared with the amount of cellulose. Furthermore, this method requires basis weight measurement, which utilizes ionizing radiation having possible adverse effects known as such, to be carried out both before and after the surface sizing.

BRIEF DESCRIPTION OF THE INVENTION

An object of this invention is to provide a novel and improved arrangement and method for determining the amount of starch to be used in surface sizing of a cellulose product.

The method according to the invention is characterized by determining the amount of starch with a transmission method utilizing IR spectroscopy in such a way that an absorption value is measured by using the absorption wavelength range of cellulose before adding starch, an absorption value is measured by using the absorption wavelength range of cellulose after having added starch, and the amount of starch is determined from the difference between said absorption values.

The arrangement according to the invention is characterized in that the arrangement comprises a first infrared source and a first detector which are arranged in such a way relative to the cellulose material that the radiation transmitted by the first infrared source is arranged to pass at least once through the cellulose material before it is received to the first detector, the first infrared source and the first detector being arranged on the production line before a starch adding station; and a second infrared source and a second detector which are arranged in such a way relative to the cellulose material that the radiation transmitted by the second infrared source is arranged to pass at least once through the cellulose material before it is received to the second detector, the second infrared source and the second detector being arranged on the production line after the starch adding station, the infrared sources and detectors being arranged to determine absorption values with a transmission method utilizing IR spectroscopy by using a wavelength range of cellulose; and a control device arranged to determine the amount of starch on the basis of the difference between the absorption values.

An idea of the invention is that the absorption wavelength range of cellulose used for example in the moisture measurements of a cellulose product is, in the solution according to the invention, also used for determining the amount of starch used in surface sizing by measuring the absorption both before and after the surface sizing.

An advantage of the invention is that it provides a significantly improved measuring accuracy, compared with conventional measuring methods. A second significant advantage of the invention is that with the method according to the invention, one measurement using ionizing radiation may become unnecessary as the basis weight of the paper does not have to be measured separately before surface sizing to implement dry weight difference measurement.

The idea of an embodiment is that a cellulose absorption wavelength range of about 2.11 µm is used for determining the amount of starch.

The idea of a second embodiment is that measurement devices used in determining the amount of starch are also used for moisture measurements of the cellulose product or for other parameter measurements of the cellulose product.

The idea of a third embodiment is that measurement of the moisture of the cellulose product uses the same measuring devices as determination of the amount of starch.

The idea of a fourth embodiment of the invention is that the measuring devices used for determining the amount of starch are also utilized in dry weight measurement. The dry weight is thus determined in such a way that the total basis weight of the cellulose product and the weight of the water in the cellulose product are measured by using the same measuring devices as in determining the amount of starch, and the dry weight is determined by subtracting the weight of the water from the total basis weight.

The idea of a fifth embodiment is that the starch determination method is used for determining starch to be used for surface-sizing a cellulose product that has a total weight of 30 to 200 g/m².

The idea of a sixth embodiment is that the measuring devices used for determining starch are also utilized for determining the ash content of the cellulose product. In this case, the ash content is determined by determining the dry weight of the cellulose product, determining the proportion of cellulose with a transmission method utilizing IR spectroscopy, and determining the ash content from the difference between the dry weight and the proportion of cellulose.

BRIEF DESCRIPTION OF THE FIGURES

Some embodiments of the invention will be explained in greater detail in the attached drawings, in which.

For the sake of clarity, embodiments of the invention are shown simplified in the figures. Similar parts are denoted with the same reference numerals in the figures.

DETAILED DESCRIPTION OF THE INVENTION

Figure 1:
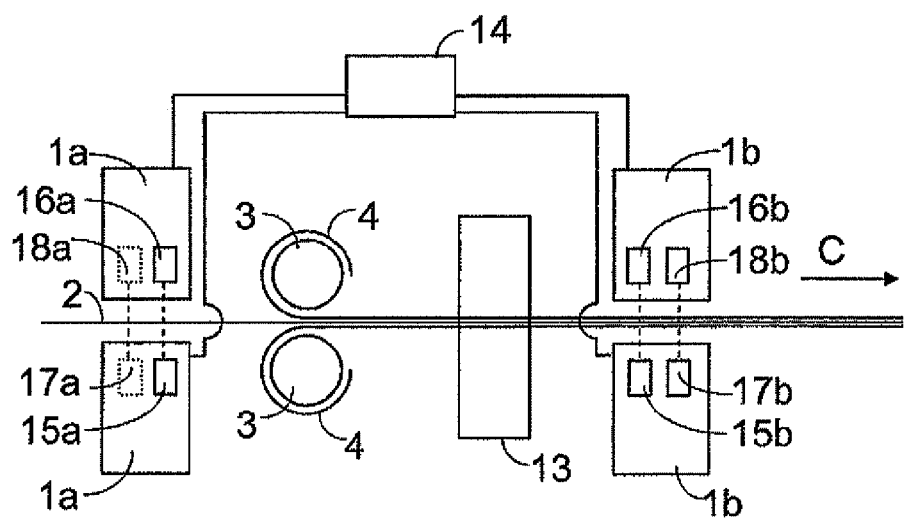
FIG. 1 shows schematically an arrangement according to the invention for measuring the amount of starch.

FIG. 1 shows schematically a typical measuring arrangement arranged in connection with surface sizing of a cellulose product, such as paper or cardboard, by showing schematically a detail of a part of a cellulose production line where the cellulose is surface-sized, as well as the related devices relevant to the measurement. In the arrangement according to the figure, starch 4 is applied to the surface of a cellulose product 2 with a technique known as such, such as film transfer technique, by means of, for example, a roll or rolls 3, such as film transfer rolls. In the embodiment according to the figure, starch is applied to the surface of the cellulose product on both sides, but in different embodiments starch may as well be added only to one side. After the surface sizing, the cellulose product is typically dried in a drying part 13, which brings out the size properties of the starch.

In FIG. 1, the cellulose product 2 moves on the production line in the direction of arrow C. Typically, production lines where the cellulose product is surface-sized comprise measuring beams 1a and 1b before a size station as well as after the size station and a drying part 13 positioned in connection with it. A measurement signal is transmitted from the measuring beams 1a and 1b to a control device 14 known as such, where the signal may be processed in various ways for instance by amplifying, filtering, converting and/or analyzing it. In applications according to the prior art, measuring beams 1a and 1b have been used for example in moisture and basis weight measurements utilizing spectroscopy.

In the solutions according to prior art, the amount of starch has typically been determined by measuring the basis weight and moisture of a cellulose product both before the surface size station and after it, as mentioned earlier. It has been possible to calculate the dry weight as the difference between the basis weight and the weight of the water, and the amount of starch has been determined as the difference between the dry weight measured after the addition of surface size and the dry weight measured before the addition of surface size. However, the uncertainty of this measuring manner has been considerable, compared with the typical small amount of starch-based surface size to be added.

Typically, ionizing beta radiation has been used for determining the basis weight because different materials absorb beta radiation in almost the same way, owing to which using beta radiation usually provides rather reliable determination of the basis weight irrespective of the composition of the material to be measured. Thus, beta radiation is transmitted from a beta radiation source 17a, 17b, part of the radiation being absorbed by the cellulose material. The part of the radiation that penetrates through the cellulose material is received by a receiver 18a, 18b. On the basis of the amount of radiation absorbed by the cellulose material, the basis weight of the material can be determined.

The weight of the water, in turn, has been typically determined by utilizing moisture measurement, which is typically based on determining the amounts of water and cellulose by utilizing IR spectroscopy. Thus, the absorption values of the water and cellulose are determined by transmitting IR radiation from a radiation source 15a, 15b and by receiving the radiation having permeated the material to be measured by means of a detector 16a, 16b. The absorption values of the radiation absorbed by the water and cellulose in the material can thus be determined at the point of the wavelength ranges corresponding to the absorption peaks of the water and cellulose. After this, the moisture can be determined by utilizing the ratio of the absorption value of the water to that of the cellulose fibre. In addition to dry weight measurement, moisture measurement carried out before the surface sizing is typically also used for controlling the initial drying of a paper machine.

In the solution according to the invention, the amount of starch can be determined directly from the wavelength range of the absorption peak common to the cellulose and the starch by means of an absorption spectrum without dry weight measurement, as explained in more detail later in the description of FIG. 3. Thus, in the solution according to the invention, the beta radiation source 17a and the receiver 18a shown by broken lines in FIG. 1 may be omitted because in this case there is typically no need to measure the total basis weight before surface sizing.

Figure 2:
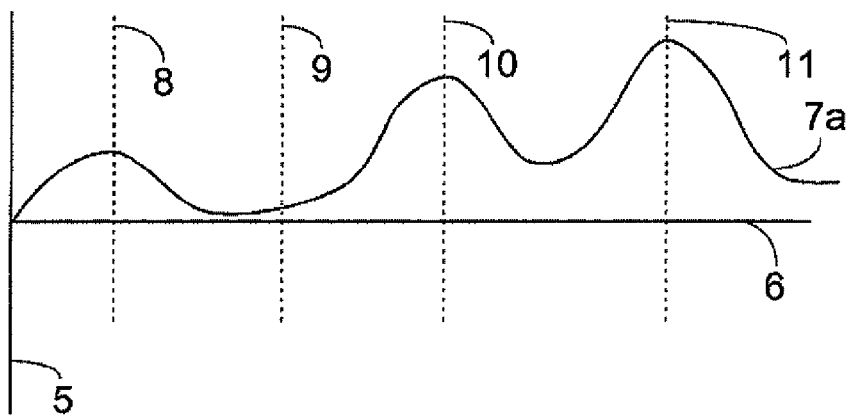
FIG. 2 shows schematically a part of the absorption spectrum of a cellulose product in the infrared wavelength range.
Figure 3:
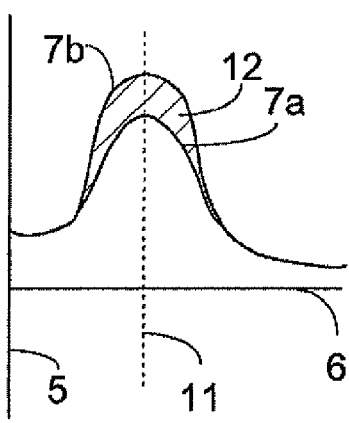
FIG. 3 shows schematically a detail of the absorption spectrum of FIG. 2 before and after coating of a cellulose product.

In embodiments of the invention, above-mentioned measuring beams 1a and 1b and wavelength ranges which have already been utilized for other measurements may preferably also be used for determining the amount of starch with methods explained in greater detail in the description of FIGS. 2 and 3. If desired, the measurement may also be performed with separate measuring devices intended for this purpose.

FIG. 2 shows schematically a part of an absorption spectrum of a cellulose product in the infrared wavelength range, the spectrum having been defined for example with the measuring arrangement shown in FIG. 1. In the figure, a y-axis 5 indicates the absorption of radiation, i.e. absorbance, an x-axis 6 indicating the wavelength. Numeral 7a in the figure indicates the absorption spectrum of the material under examination, in this case the cellulose product, defined with the transmission method; in other words it indicates how much passing through the material has absorbed radiation in each wavelength range. The absorption peaks at broken lines 8 (wavelength about 1.45 μm) and 10 (wavelength about 1.9 μm) are absorption peaks of water. The absorption value at a wavelength of about 1.8 μm, indicated by broken line 9 in the figure, can often be used in these types of measurements with cellulose products as a reference value in which no component contained by the object of measurement has a specific absorption band. At broken line 11, i.e. at a wavelength of about 2.11 μm, there is, in turn, the absorption peak of cellulose and starch, which is utilized in determining the amount of starch according to this invention, shown in more detail in FIG. 3. It is to be noted that the absorption peaks shown in FIGS. 2 and 3 are only intended to illustrate the invention, and their purpose is not to correspond the absorption spectrum of any cellulose material as such.

FIG. 3 shows a part of the absorption spectrum of a cellulose product shown in FIG. 2 at broken line 11, i.e. at a wavelength of about 2.11 μm, i.e. at the absorption peak of cellulose and starch. Deviating from FIG. 2, FIG. 3 shows both the absorption spectrum 7a based on measurement before the surface sizing, i.e. at the measuring beam 1a in the embodiment of FIG. 1, and an absorption spectrum 7b based on measurement after the surface sizing, i.e. at the measuring beam 1b in the embodiment of FIG. 1.

Determination of the absorption spectrum in the measuring beams 1a and 1b takes place, in practice, with a transmission method in such a way, for example, that the radiation of the first and the second infrared source 15a, 15b is divided into different wavelengths with a rotating filter disc, for example, and the radiation is directed to pass through the cellulose material to be measured, moving on the production line, once or more times by means of mirroring surfaces, for example. The radiation having permeated the cellulose material is received with what are called the first and the second detector 16a, 16b, and the obtained signal is processed with the control device 14 by means of methods known as such to convert the absorption spectrum to absorption values that can be measured.

In the solution according to the invention, the absorption spectrum 7a according to FIG. 3 can be determined in a manner described above by arranging the first infrared source 15a and the first detector 16a at the measuring beam 1a on the production line before the starch adding station. The absorption spectrum 7b, in turn, can be determined by arranging the second infrared source 15b and the second detector 16b at the measuring beam 1b on the production line after the starch adding station. The amount of cellulose can thus be determined from the absorption spectrum 7a at the measuring beam 1a, i.e. before adding surface size to the surface of the cellulose product, on the basis of the absorption of infrared radiation caused by the material at a wavelength of about 2.11 μm, i.e. at the absorption peak of cellulose and starch. From the absorption spectrum 7b, in turn, the total amount of cellulose and starch after the adding of surface size can be determined because the absorption values of cellulose and starch are summed up at the absorption peak common to them, positioned at the wavelength 11. Subsequently, the amount of starch can be determined on the basis of the difference 12 between the absorption values 7a, 7b at the wavelength 11. Thanks to new measuring devices with improved measuring accuracy and to a decrease in the number of separate measurements which are required for determining the amount of starch and increase the measuring uncertainty, the solution according to the invention allows the measuring uncertainty to be significantly reduced in determining the amount of starch. The advantages of this determination method are emphasized particularly in connection with printing paper products having a total weight of 30 to 200 g/m².

In the embodiments of the invention, determining the absorption spectrum is not necessary over a wider wavelength range. In different embodiments, the absorption value of the material can be determined directly at a particular wavelength before adding starch and after it, after which the amount of added starch can be determined on the basis of the difference between these absorption values.

In an embodiment of the invention, the measuring devices used for determining the amount of starch may preferably also be used for determining the ash content of a cellulose product. In this case, the total basis weight and the weight of the water are determined first, and the dry weight is determined from these by subtracting the weight of the water from the total basis weight. Infrared measurement is used to measure the proportion of cellulose (and starch if the measurements are performed after surface sizing), and the ash content is determined with equation AW=OD−CeW, where AW is the ash weight, OD is the dry weight and CeW is the weight of the cellulose. The ash content as per cents ASH % can be calculated from this with equation ASH %=(AW/OD)*100.

In the solution according to the invention, the amount of starch can be determined with such measuring devices and by using such wavelength ranges which are often already in use on cellulose product production lines using surface sizing. Thus, no separate measuring devices for carrying out this determination are needed. Unless basis weight measurement before adding surface size is needed for other purposes, one measurement using ionizing radiation can be eliminated in the solution according to the invention. In contrast, the solution according to the invention can exploit measurements that it has in common with moisture measurement, which is usually necessary in any case, both before and after the surface sizing.

In some cases, features disclosed in this application may be used as such, irrespective of other features. On the other hand, features disclosed in this application may, if required, be combined to form various combinations. The ash content, for example, may be determined without determining the amount of starch at the same time.

The drawings and the related description are only intended to illustrate the idea of the invention. Details of the invention may vary within the scope of the claims.

The invention claimed is:

1. A method of determining an amount of starch used in surface-sizing a cellulose product, comprising:
   determining the amount of starch with a transmission method utilizing IR spectroscopy in such a way that a first absorption value is measured before adding starch, a second absorption value is measured after having added starch, and the amount of starch is determined from the difference between said absorption values, wherein:
   the first absorption value is used to determine a first amount of cellulose based on absorption of infrared radiation by the cellulose product at an absorption wavelength range of cellulose and starch, the second absorption value is used to determine a second amount of cellulose and starch based on absorption of infrared radiation by the cellulose product at the absorption wavelength range of cellulose and starch, and the amount of starch is determined from the difference between the first amount of cellulose and the second amount of cellulose and starch.

2. A method according to claim 1, further comprising:
using a wavelength range of about 2.11 μm for determining the amount of starch.

3. A method according to claim 1, further comprising:
measuring the moisture of the cellulose product by using the same measuring devices as in determining the amount of starch.

4. A method according to claim 3, further comprising:
determining the dry weight of the cellulose product in such a way that the total basis weight of the cellulose product is measured, the weight of the water in the cellulose product is measured by using the same measuring devices as in determining the amount of starch, and the dry weight is determined by subtracting the weight of the water from the total basis weight.

5. A method according to claim 1, wherein the total weight of the cellulose product is substantially 30 to 200 g/m².

6. A method according to claim 1, further comprising:
determining the ash content of the cellulose product in such a way that the dry weight of the cellulose product is determined, the proportion of cellulose is determined with a transmission method utilizing IR spectroscopy, and the ash content is determined from the difference between the dry weight and the proportion of cellulose.

7. An arrangement for determining an amount of starch used in coating a cellulose product with a transmission method utilizing IR spectroscopy by using an absorption wavelength range of cellulose, the arrangement comprising:

a first infrared source and a first detector that are configured relative to the cellulose product such that the radiation transmitted by the first infrared source is arranged to pass at least once through the cellulose product before the radiation is received by the first detector, the first infrared source and the first detector being arranged on the production line before a starch adding station;

the first detector being configured to measure a first absorption value in order to determine a first amount of cellulose based on absorption of infrared radiation by the cellulose product at an absorption wavelength range of cellulose and starch;

a second infrared source and a second detector that are configured relative to the cellulose product such that the radiation transmitted by the second infrared source is arranged to pass at least once through the cellulose product before the radiation is received by the second detector, the second infrared source and the second detector being arranged on the production line after the starch adding station;

the second detector being configured to measure a second absorption value that is used to determine a second amount of cellulose and starch based on absorption of infrared radiation by the cellulose product at the absorption wavelength range of cellulose and starch; and a control device arranged to determine the amount of starch on the basis of the difference between the first amount of cellulose and the second amount of cellulose and starch.

8. An arrangement according to claim 7, wherein the devices are arranged to use a wavelength range of about 2.11 μm for determining the amount of starch.

9. An arrangement according to claim 7, wherein measuring devices used for determining the amount of starch are also arranged to be used for moisture measurements of the cellulose product or for other parameter measurements of the cellulose product.

10. An arrangement according to claim 7, wherein measuring devices used for determining starch are also arranged to be utilized in dry weight measurement.

11. An arrangement according to claim 7, wherein the total weight of the cellulose product is substantially 30 to 200 g/m².

12. An arrangement according to claim 7, wherein the measuring devices used for determining starch are also arranged to be used for determining the ash content of the cellulose product.

* * * * *